United States Patent [19]
Aldwin et al.

[11] Patent Number: 5,491,074
[45] Date of Patent: Feb. 13, 1996

[54] ASSOCIATION PEPTIDES

[75] Inventors: Lois Aldwin, San Mateo; Mark Madden, Davis; Willem P. C. Stemmer, Los Gatos, all of Calif.

[73] Assignee: Affymax Technologies NV, Curacao, Netherlands Antilles

[21] Appl. No.: 67,387

[22] Filed: May 24, 1993

Related U.S. Application Data

[63] Continuation-in-part of Ser. No. 171,893, Dec. 22, 1993, which is a continuation of Ser. No. 43,459, Apr. 1, 1993, abandoned.

[51] Int. Cl.$^6$ ................................................. C12P 21/02
[52] U.S. Cl. ........................... 435/69.7; 435/6; 435/7.1; 435/7.8; 435/69.6; 530/350; 530/387.1
[58] Field of Search .................................. 435/6, 7.1, 7.2, 435/7.6, 7.8, 69.7, 69.6; 530/350, 387.1

[56] References Cited

PUBLICATIONS

Plueckthun et al. (1990) ICSU Short Rep. vol. 10: 94–95 (Abstr. only).
Tawfik et al. (1993) PNAS vol. 90: 373–377.
Vinayek et al, Methods in Enzymology 191, 1990, pp. 609–639.
Srere et al, Methods in Enzymology 182, 1990, pp. 539–551.
Bodenmuller et al., 1983, EMBO J. 5(8):1825–1829 The nueropeptide head activator loses its biological activity by dimerization.
Blalock et al., 31 May 1984, Biochem. Biophys. res. Comm. 121(1):203–207 Hydropathic Anti–Complementary of Amino Acids Based on the Genetic Code.
Shai et al., 1987, Biochem. 26:669–675 Anti–Sense peptide recognition of sense peptides: Direct quantitive characterization wht the ribonuclease S–peptide system using analytical high–peformance affinity chromatography.
Shai 'et al., 1989, Biochem. 28:8804–8811 Antisense peptide recognition of sense peptides: sequence simplification and evaluation of forces underlying the interaction.
Goldstein et al., Jan. 1989, Proc. Natl. Acad. Sci. USA 86:42–45 Is there a relationship between DNA sequences encoding peptide ligands and their receptors?.
Blondel et al., 1991, Protein Eng. 4 (4):457–461 Engineering the quaternary structure of an exported protein with a leucine zipper.
Lu et al., May 1991, Proc. Natl. Acad. Sci. USA 88: 3642–3646 Affinity capture of [Arg8] vasopressin–receptor complex using immobilized antisense peptide.
Cowley et al., 1992, Eur. J. Biochem. 205: 1099–1106 Structure of neuropeptide Y dimer in solution.
Ghadiri et al., 1992, J. Am. Chem. Soc. 114:825–831 A convergent approach to protein design. Metal Ion–assisted spontaneous self–assembly of a polypeptide into a triple–helix bundle protein.
Nelsen, L., Jul./Aug. 1992, The MIT Report, Case No. 5824W: 6, p. 6 New Inventions: Amino acid sequence of de novo design that function as molecular velcro.

*Primary Examiner*—Mindy Fleisher
*Assistant Examiner*—Philip W. Carter
*Attorney, Agent, or Firm*—Lauren L. Stevens; Kevin R. Kaster

[57] ABSTRACT

Peptides that form lightly associated homodimers can be used to form dimers and multimers of other molecules and molecular motifs of interest. These association peptides can dimerize regardless of whether motifs are added to the amino-terminus of the peptide, or the carboxy terminus of the peptide, although additions to the carboxy-terminus of the association peptides require the presence of certain acidic residues.

10 Claims, No Drawings

ASSOCIATION PEPTIDES

CROSS-REFERENCE TO RELATED APPLICATIONS

The present application is a continuation-in-part of U.S. patent application U.S. Ser. No. 08/171,893, filed Dec. 22, 1993, which is a file wrapper continuation of U.S. Ser. No. 043,459, filed Apr. 1, 1993, now abandoned, incorporated herein by reference.

BACKGROUND OF THE INVENTION

1. Field of the Invention

The association peptides and methods of the invention relate to the fields of molecular biology, polymer chemistry, biotechnology, and pharmacology.

2. Description of Related Art

Bodenmuller et al., 1983, EMBO 5 (8): 1825–1829, incorporated herein by reference, shows that the neuropeptide head activator (HA) dimerizes to yield a biologically inactive form of the peptide at concentrations as low as $10^{-13}$M, indicating extremely high binding affinity. The authors observed that a fragment containing the last six amino acids of this peptide's carboxy terminus (SKVILF) (SEQ.ID NO:1) resulted in dimers that were even "more stable" than the HA itself. The article also reports the construction of HA analogs that lack the SKVILF (SEQ.ID NO:1) motif and do not dimerize and that alteration of the phenylalanine residue at the carboxy-terminus, as well as alteration of residues attached to the amino-terminus, of SKVILF (SEQ.ID NO;1) in the Ha results in the loss of dimerization activity. While peptides capable of dimerization could be quite valuable in many molecular biology methods, these results suggested that the HA peptide could not be attached to a second molecule for purposes of dimerizing the second molecule.

One important class of molecular biology methods where dimerization peptides would be of value is the class of methods for generating and screening molecular diversity. The ability to synthesize DNA chemically has made possible the construction of extremely large collections of nucleic acids, peptides, proteins, and other polymers. These collections can be screened to isolate ligands that bind biological receptors or to identify catalysts that mediate a desired reaction by binding to a substrate. In recent years, several methods have been developed for generating such libraries of compounds for screening. These methods can be grouped for discussion into methods that utilize living organisms and methods that rely on in vitro chemical synthesis.

One important method in the former category involves the display of a biological molecule, such as a peptide, antibody, or other protein (collectively referred to as "(poly)peptide") on the surface of a phage or cell. These methods typically involve establishing a physical or logical connection between each (poly)peptide and the nucleic acid that encodes the (poly)peptide; perhaps the best known method in this category involves the presentation of a (poly)peptide on the surface of a filamentous phage. The phage can be incubated with an immobilized receptor of interest, so that phage that present a (poly)peptide that binds to the receptor can be separated from phage that do not. After several rounds of affinity enrichment and phage replication, followed by isolation of the phage that bind and sequence determination of the phage nucleic acid, this method allows one to identify the sequence of (poly)peptide ligands for the receptor. Such methods are described in more detail in PCT patent publication Nos. 91/17271; 91/18980, and 91/19818, each of which is incorporated herein by reference.

Another important recombinant method for the display of (poly)peptide ligands involves the production of a fusion protein composed of a protein that specifically binds to DNA and the potential (poly)peptide ligand. In one embodiment of this method, the library of (poly)peptides is produced by transforming recombinant host cells with a vector that encodes a lac repressor/(poly)peptide fusion protein and contains a lac operator sequence. When the transformed host cells are cultured under conditions that allow for expression of the fusion protein, the fusion protein binds to the vector that encodes the fusion protein. Upon lysis of the host cells, the fusion protein/vector complexes can be screened against a receptor in much the same way the phage are screened in the phage-based display method. See U.S. patent application Ser. No. 963,321, filed Oct. 15, 1992, which is a continuation-in-part of Ser. No. 778,233, filed Oct. 16, 1991, and Ser. No. 08/038,726, filed Mar. 25, 1993, inventor W. P. C. Stemmer, each of which is incorporated herein by reference.

In contrast to the recombinant methods, in vitro chemical synthesis provides a method for generating libraries of compounds, without the use of living organisms, that can be screened for ability to bind to a receptor. Although in vitro methods have been used for quite some time in the pharmaceutical industry to identify potential drugs, recently developed methods have focused on rapidly and efficiently generating and screening large numbers of compounds. One early method involves the synthesis of peptides on a set of pins or rods. See PCT patent publication Nos. 84/03506 and 84/03564, each of which is incorporated herein by reference. Another method involves the use of a synthesis resin or beads and a variety of flow-through containers into which the beads are placed. The containers are then exposed to monomer-coupling solutions and labeled to indicate the monomer coupling reactions to which the container has been exposed. See U.S. Pat. No. 4,631,211, incorporated herein by reference. A related method dispenses with the labeling step and separate containers for each peptide to achieve greater diversity at the cost of easy identification of a particular ligand of interest. In this method, the synthesis beads are pooled and redistributed after each set of monomer coupling reactions. After screening with a receptor, the ligands on a bead of interest must be identified by removing the ligand from the bead and determining the molecular structure of the ligand. See PCT patent publication No. 92/00091, incorporated herein by reference.

A significant improvement over this latter method involves tagging each bead with an identifier tag, such as an oligonucleotide, so as to facilitate ligand identification. This method is described in U.S. patent application Ser. No. 946,239, filed Sep. 16, 1992, which is a continuation-in-part of Ser. No. 762,522, filed Sep. 18, 1991, each of which is incorporated herein by reference. Another powerful method for generating large collections of compounds addresses the ligand identification problem by forming arrays of different compounds in a manner that places each different compound of the array at a discrete, predefined location. The location identifies each ligand. This method, called "very large scale immobilized polymer synthesis," is described in U.S. patent No. 5,143,854; PCT patent publication Nos. 90/15070 and 92/10092; U.S. patent application Ser. No. 624,120, filed Dec. 6, 1990; Fodor et al., 15 Feb. 1991, Science 251:767–773; Dower and Fodor, 1991, Ann. Rep. Med. Chem. 26:271–280; and U.S. patent application Ser. No.

805,727, filed Dec. 6, 1991, each of which is incorporated herein by reference.

Other systems for generating libraries of compounds have aspects of both the recombinant and in vitro chemical synthesis methods. In these hybrid methods, biological enzymes or enzyme complexes play an important role in generating the compounds, but no living organisms or cells are directly used. For example, RNA molecules with the ability to bind a particular protein (see Tuerk and Gold, 1990, Science 249:505–510; Beaudry et al., 31 Jul. 1992, Science 257:635–641; Green et al., Feb. 1991, Methods-:Meth. Enz. 2 (1): 75–86; and PCT patent publication No. 91/19813, each of which is incorporated herein by reference) or a dye (see Ellington and Szostak, 1990, Nature 346:818–822, incorporated herein by reference) have been selected by alternate rounds of affinity selection and PCR amplification. A similar technique was used to determine the DNA sequences that bind a human transcription factor (see Thiesen and Bach, 1990, Nucl. Acids Res. 18:3203–3209, Beaudry and Joyce, 31 Jul. 1992, Science 257:635–641, and PCT patent publication Nos. 92/05285 and 92/14843, each of which is incorporated herein by reference). In similar fashion, the technique of in vitro translation has been used to synthesize proteins of interest (see PCT patent publication Nos. 88/08453, 90/05785, 90/07003, and 91/02076, each of which is incorporated herein by reference); this technique has also been proposed as a method to generate large libraries of peptides. See PCT patent publication Nos. 91/05058 and 92/02536, each of which is incorporated herein by reference.

There remains a need for improved methods of and reagents for constructing and screening libraries of compounds in addition to the methods described above. For instance, many monovalent receptors do not bind to relatively low (10 μm) affinity ligands presented using some of the systems described above, and a means for dimerizing such receptors would be helpful. Blondel and Bedouelle, 1991, Protein Engineering 4:457–461, incorporated herein by reference, reports the design of a dimeric form of the maltose binding protein (MBP) that included a 33-residue leucine zipper motif; other methods for dimerizing proteins would be helpful, especially if the methods produced very stable dimers. Conversely, some receptors may require dimeric ligands, and a generic means for dimerizing ligands would be useful in identifying ligands that bind to such receptors. Ghadiri et al., 1992, J. Am. Chem. Soc. 114:825–831, incorporated herein by reference, reports a method for assembling a small peptide into a multimeric structure by incorporation of a 2,2'-bipyridine moiety in the peptide and the use of a metal ion to assist assembly. Simpler methods for forming multimeric peptide sequences are needed.

In addition, catalytic molecules are important in many biological processes, yet the methods above are not all ideally suited for screening to identify such compounds. Over the past several years, many scientists have proposed that catalytic biological molecules, especially catalytic antibodies, will prove invaluable in manufacturing processes for chemicals. See, e.g., PCT patent publication Nos. 90/05746, 90/05749, 90/05785, and 92/01781; U.S. Pat. No. 5,190, 865; and Tawfik et al., Jan. 1993, Proc. Natl. Acad. Sci. USA 90:373–377, each of which is incorporated herein by reference. See also U.S. patent application Ser. No. 043,459, previously incorporated herein by reference. The association peptides of the present invention will prove valuable in constructing and identifying such catalytic molecules as well as in generating and screening large libraries of compounds.

SUMMARY OF THE INVENTION

The present invention provides peptides that form tightly associated dimers and can be used to dimerize or otherwise aggregate other compounds containing motifs of interest. The peptides can dimerize even when present in fusion proteins comprising the peptide and a compound added at the amino-terminus or the carboxy-terminus of the peptide. The dimerizable peptides and proteins of the invention are very stable, exhibit high binding affinities, and are useful in a wide variety of applications.

In a preferred embodiment, the association peptide is SKVILF (SEQ.ID NO:1), and the molecules to be joined together are selected from the group consisting of carbohydrates, nucleic acids, peptides, polypeptides, and proteins, such as antibodies, antibody fragments, or other receptors, and are fused to the amino-terminus, optionally via a flexible linker or spacer such as GGPP, (SEQ.ID NO:2), PPGG (SEQ.ID NO:3), or GGPPGG (SEQ.ID NO:4), of the association peptide. In another preferred embodiment, the association peptide is SKVILF (SEQ.ID NO;1), and the molecules to be joined together are attached to the carboxyl terminus of the peptide by a linker or other attachment means so that a free carboxyl group is located in the resulting peptide-molecule fusion complex immediately following the F residue of the association peptide.

DETAILED DESCRIPTION OF THE INVENTION

I. Definitions

For purposes of understanding the present invention, the following terms are defined.

Amino acid residues in peptides are abbreviated as follows: Phenylalanine is Phe or F; Leucine is Leu or L; Isoleucine is Ile or I; Methionine is Met or M; Valine is Val or V; Serine is Ser or S; Proline is Pro or P; Threonine is Thr or T; Alanine is Ala or A; Tyrosine is Tyr or Y; Histidine is His or H; Glutamine is Gln or Q; Asparagine is Asn or N; Lysine is Lys or K; Aspartic Acid is Asp or D; Glutamic Acid is Glu or E; Cysteine is Cys or C; Tryptophan is Trp or W; Arginine is Arg or R; and Glycine is Gly or G.

The term "antibody" refers to antibodies and antibody fragments that retain the ability to bind the epitope that the intact antibody binds, whether the antibody or fragment is produced by hybridoma cell lines, by immunization to elicit a polyclonal antibody response, or by recombinant host cells that have been transformed with a recombinant DNA expression vector that encodes the antibody or antibody fragment.

The term "antigen" refers to a molecule that induces the formation of an antibody or binds specifically to the antigen-binding sites of an antibody.

The term "catalytic molecule" refers to a compound, such as an antibody, antibody fragment, or enzyme, that is capable of enhancing the rate of a chemical reaction. The catalytic molecule may, but typically, does not, enter into the chemical reaction and may be, but typically is not, consumed in the reaction.

The term "effective amount" refers to an amount sufficient to induce a desired result.

The term "epitope" refers to that portion of an antigen that interacts with an antibody.

The term "host cell" refers to a eukaryotic or procaryotic cell or group of cells that can be or has been transformed by a recombinant DNA vector. For most purposes of the present invention, procaryotic host cells are preferred.

The term "ligand" refers to a molecule that is recognized by a particular receptor. Any agent bound by or reacting with a receptor is called a "ligand," so the term encompasses the substrate of an enzyme and the reactants of a catalyzed reaction. The term "ligand" does not imply any particular molecular size or other structural or compositional feature other than that the substance in question is capable of binding or otherwise interacting with a receptor, enzyme, or catalyst. A "ligand" may serve either as the natural ligand to which the receptor binds or as a functional analogue that may act as an agonist or antagonist.

The term "linker" or "spacer" refers to a molecule or group of molecules (such as a monomer or polymer) that connects two molecules and often serves to place the two molecules in a preferred configuration, e.g., so that a ligand can bind to a receptor with minimal steric hindrance.

The term "monomer" refers to any member of the set of molecules that can be joined together to form an oligomer or polymer. The set of monomers useful in the present invention includes, but is not restricted to, for the example of (poly)peptide synthesis, the set of L-amino acids, D-amino acids, or synthetic amino acids. As used herein, "monomer" refers to any member of a basis set for synthesis of an oligomer. For example, dimers of L-amino acids form a basis set of 400 "monomers" for synthesis of polypeptides. Different basis sets of monomers may be used at successive steps in the synthesis of a polymer. The term "monomer" also refers to a chemical subunit that can be combined with a different chemical subunit to form a compound larger than either subunit alone.

The term "oligomer" or "polymer" refers to the compounds formed by the chemical or enzymatic addition of two or more monomers to one another. Such oligomers include, for example, both linear, cyclic, and branched polymers of nucleic acids and peptides, which peptides can contain alpha-, beta-, or omega-amino acids.

The term "oligonucleotide" refers to a single-stranded DNA or RNA polymer containing deoxyribonucleotides or ribonucleotides or analogs of either. Suitable oligonucleotides may be prepared by the phosphoramidite method described by Beaucage et al., 1981, Tetr. Lett. 22:1859–1862, or by the triester method, according to Matteucci et al., 1981, L Am. Chem. Soc. 103:3185, or by other methods, such as by using commercially available, automated oligonucleotide synthesizers.

The term "operably linked" refers to the placement of one nucleic acid into a functional relationship with another nucleic acid. For instance, a promoter is "operably linked" to a coding sequence if the promoter causes the transcription of the coding sequence. Generally, "operably linked" means that the DNA sequences being linked are contiguous and, where necessary to join two peptide or protein coding regions, in reading frame with one another.

The term "peptide" refers to an oligomer in which the monomers are amino acids (usually alpha-amino acids) joined together through amide bonds. Peptides are two or more amino acid monomers long, but more often are between 5 to 10 amino acid monomers long and can be even longer, i.e. up to 20 amino acids or more, although peptides longer than 20 amino acids are more likely to be called "polypeptides." The term "protein" is well known in the art and usually refers to a very large polypeptide, or set of associated homologous or heterologous polypeptides, that has some biological function. For purposes of the present invention the terms "peptide," "polypeptide," and "protein" are largely interchangeable as all three types can be attached to an association peptide by similar methodology and so are collectively referred to as "(poly)peptides."

The term "random peptide" refers to an oligomer composed of two or more amino acid monomers and constructed by a means with which one does not entirely preselect the specific sequence of any particular oligomer.

The term "random peptide library" refers not only to a set of recombinant DNA vectors that encodes a set of random peptides, but also to the set of random peptides encoded by those vectors, as well as the set of fusion proteins containing those random peptides. The term "protein library" has a meaning similar to "random peptide library," but the different library members differ with respect to the amino acid sequence of, or coding sequence for, the protein of interest, so that the library serves as a collection of related but different versions of the same protein.

The term "receptor" refers to a molecule that has an affinity for a given ligand. Receptors may be naturally-occurring or synthetic molecules. Receptors can be employed in the present invention in their unaltered natural or isolated state or as aggregates with other species or in some modified or recombinant form. Examples of receptors include, but are not restricted to, antibodies, cell membrane receptors, monoclonal antibodies, antisera reactive with specific antigenic determinants (such as on viruses, cells, or other materials), polynucleotides, nucleic acids, lectins, polysaccharides, cells, cellular membranes, viruses, and organelles. Receptors are sometimes referred to in the art as "anti-ligands." A "ligand-receptor pair" is formed when two macromolecules have combined through molecular recognition to form a complex.

The terms "recombinant DNA cloning vector" and "recombinant DNA expression vector" refer to a DNA or RNA molecule that encodes a useful function and can either be used to transform a host cell or be introduced into a cell-free translation system to produce a protein encoded by the vector. For purposes of the present invention, a cloning vector typically serves primarily as an intermediate in the construction of an expression vector; the latter vector is used to transform or transfect a host cell (or is introduced into a cell-free transcription and translation system) so that the transformed host cell (or cell-free transcription and translation system) produces a protein or other product encoded by the vector. Such vectors are typically "plasmids," which, for purposes of the present invention, are vectors that can be extrachromosomally maintained in a host cell, but can also be vectors that integrate into the genome of a host cell. Those of skill in the art may refer to "cloning vectors", as defined herein, as "vectors" and to "expression vectors," as defined herein," as "plasmids."

The term "reporter group" or "tag" refers to an atom, compound, or biological molecule or complex that can be readily detected when attached to other molecules and exploited in chemical separation processes. Typical reporter groups include either member of receptor-ligand pairs, such as antibody-epitope, avidin-biotin, or complementary nucleic acid strand pairs. A reporter group can also be a fluorescent or radioactive atom or a compound continuing one or more such atoms.

The term "substrate" refers to a ligand or a receptor or a substrate of an enzyme.

The term "solid support" refers to a material having a rigid or semi-rigid surface. Such materials will preferably take the form of small beads, pellets, disks, chips, or wafers, although other forms may be used. In some embodiments, at least one surface of the substrate will be substantially flat. The term "surface" refers to any generally two-dimensional structure on a solid substrate and may have steps, ridges, kinks, terraces, and the like without ceasing to be a surface.

The term "synthetic" refers to production by in vitro chemical or enzymatic synthesis.

II. The Invention

The present invention provides novel association peptides that can be used in a wide variety of methods to join two or more molecules together. In a preferred embodiment, the association peptide is SKVILF (SEQ.ID NO:1), and the molecules to be joined together are selected from the group consisting of carbohydrates, nucleic acids, peptides, polypeptides, and proteins, such as antibodies, antibody fragments, or other receptors, and are fused to the amino-terminus, optionally via a flexible linker or spacer such as GGPP(SEQ.ID NO:2), PPGG(SEQ.ID NO:3), or GGP-PGG(SEQ.ID NO:4), of the association peptide. In another preferred embodiment, the association peptide is SKVILF-(SEQ.ID NO:1), and the molecules to be joined together are attached to the carboxyl terminus of the peptide by a linker or other attachment means so that a free carboxyl group is located in the resulting peptide-molecule fusion complex immediately following the F residue of the association peptide.

These association peptides can be used in a wide variety of applications. In one preferred embodiment, the association peptides can be used to dimerize a peptide or protein. For smaller peptides, one can make the monomeric, association peptide-containing molecules of the invention by well known peptide synthesis techniques using commercially available instruments. For larger peptides, polypeptides, and proteins, one may more conveniently use recombinant DNA expression vectors and methods to produce a recombinant fusion protein that comprises the association peptide and the polypeptide or protein to be dimerized. In this fashion, one can produce multivalent receptors for use in drug screening; such multivalent receptors are especially useful in screening an array of low affinity ligands for ligands that bind the receptor (see U.S. Pat. No. 5,143,854, incorporated herein by reference).

The association peptides of the invention may also be used to create novel ligands. In an illustrative embodiment, the association peptides are used in a novel method of the invention that involves "shuffling" of combinatorially associated random peptide libraries (such as the phage-based random peptide libraries discussed in the "Background" section above) to obtain collections of molecules with as many as $10^{15}$ different members. In this method, combinatorial association is used to obtain great total diversity from two (or more) smaller libraries, as has been done, in a less efficient manner, with antibody heavy and light chain libraries in $E.\ coli$. This latter work shows that one can combinatorially associate a tagged, amplifiable library (VH-phage), with an untagged library (free VL chains), pick the best VH, express the VH as free chains, and use these free chains to select the best VL-chains from a VL-phage library. The total complexity screened can be as high as the product the two library sizes (approximately $10^8 \times 10^8 = 10^{16}$).

A primary goal of random peptide library generating and screening methods is to increase the effective size of the library. Theoretically, one should be able to obtain more, and higher affinity, ligands with larger libraries. Phage (and other random peptide) libraries typically consist of $10^{12}$ total particles with $10^9$ different binding sites. The effective number of different binding sites can be increased by combinatorial association with a library of synthetic peptides. High affinity peptide-protein association is provided by the dimerization of two copies of an association peptide of the invention, one copy of which is present in the random peptide containing library fusion protein and one copy of which is present in each member of a collection of random synthetic peptides.

In a phage-based random peptide library, in which the random peptide is displayed as a fusion with a coat protein, such as the pIII or pVIII coat proteins, one can assume there are five copies of the pIII fusion protein per phage. The present method produces, for a library of $10^9$ different phage ($10_{12}$ total copies), and upon the addition of $5 \times 10^9$ different peptides, a diversity of $5 \times 10^{12}$ different binding sites. This library is screened, and the best (for example) $10^3$ phage are amplified to $10^{12}$ total copies. A library of synthetic peptides (preferably of $>10^9$ diversity) is again added, and a reshuffled library of $5 \times 10^{12}$ different binding sites is obtained and screened. These steps can be repeated as necessary. The best (for example) 5–10 phage clones are sequenced, and the 5–10 synthetic peptides corresponding to these DNA sequences are synthesized (peptide set A), each with an association peptide of the invention attached. One of two libraries is now fixed, with the format shifted from phage to synthetic peptide. These best peptide sequences are now associated with the other library, which is now on phage (a new aliquot of the same library as before). Again, the $10^9$ different phage are associated with the 5–10 different synthetic peptides, and the best 5–10 phage are selected. After sequencing of the clones of this second phage library, 5–10 different peptides are synthesized (peptide set B) each with an association peptide of the invention attached. Association of peptide set A with peptide set B will result in 25–100 different molecules, which can be evaluated individually.

The association peptides of the invention can also be used to attach a substrate non-covalently to a molecular catalyst, as described in U.S. patent application Ser. No. 043,459, supra, or to label a substance via a labeled association peptide. The association peptides of the invention can also be used to modify the properties of a first molecule by attaching a second molecule capable of conferring the desired properties (i.e., size, charge, hydrophobicity, etc.) to the first via an association peptide interaction. The association peptides of the invention can be used as an affinity purification reagent to purify substances that contain a complementary association peptide. In addition, the association peptides of the invention can be used to introduce loops into a polypeptide of interest. In this embodiment, a pair of association peptides is incorporated into the molecular target so that when the pair of association peptides interact intramolecularly, a loop is formed in the target molecule. In a similar fashion, one can bind two alpha-helical polypeptides together side-by-side by placing association peptides at both ends of each alpha-helical polypeptide and forming intermolecular association peptide dimers. In such ways, the present invention can be used to create molecular structures of great diversity. In fact, the association peptides of the invention can be polymerized to make linear polymers or polymeric gels. A polymeric gel could be used to trap a drug or other substance for purposes of controlled delivery.

Although the SKVILF (SEQ.ID NO:1) peptide is a preferred association peptide of the invention, other peptides, such as magainin peptide, metenkephalin, neurotensin, substance P, MHC peptide (see Stagsted et al., 1990, Cell 62: 297–307, incorporated herein by reference), or the neuropeptide Y, which is a 36 amino acid peptide that can self-dimerize (see Cowley et al., 1992, Eur. J. Biochem. 205: 1099–1106, incorporated herein by reference), can be used in the present methods. Heterologous association peptides, i.e., two different peptides that associate to form a heterodimer, such as "anti-sense" peptides, can also be used (see Blalock and Smith, 31 May 1984, Biochem. Biophys. Res. Comm. 121 (1): 203–207; Shai et al., 1987, Biochem.

26: 669–675; Goldstein et al., January 1989, Proc. Natl. Acad. Sci. USA 86: 42–45; Shai et al., 1989, Biochem. 28: 8804–8811; and Lu et al., May 1991, Proc. Natl. Acad. Sci. USA 88: 3642–3646, each of which is incorporated herein by reference. In general, these peptides have one, two, or more copies of the motif defined by +XXX–, where "+" is a positively charged amino acid; "–" is a negatively charged amino acid; and each "X" can independently be any amino acid.

One can also use a variety of peptide library generating and screening methods, such as those discussed in the "Background" section above, to identify association peptides of the invention. For instance, one could immobilize a peptide on a solid support such as a bead or chromatographic resin or glass plate, and then incubate the solid support with a random peptide library. Non-binding library members would be washed from the support, and then, specific binding members would be removed and identified, thus identifying association peptide pairs, one member of which would be the peptide that was on the solid support during the screening step.

buffer (100 mM NaCl and 10 mM Tris, pH=7.5), and 0.2–0.4 mL of sample were loaded onto a Bio-Gel P-4 column (1.5×48 cm). After the first 25 mL eluted from the column, fractions were collected (67 drops per fraction), and each fraction was analyzed for peptide with a Hewlett-Packard spectrophotometer (at 220 nm, 260 nm, and 280 nm).

Peptides EPPGGSKVILF (SEQ.ID NO:8), YGGFLPPGGSKVILF (SEQ.ID NO:9), and FGSSGWVLPSPPGGSKVILF (SEQ.ID NO:10), were eluted from pre-equilibrated Bio-Gel P-4 columns (BioRad) using either buffer "A" (0.1M NaCl, 10 mM Tris, pH=7.5), buffer "B" (1M ammonium sulfate, 10 mM Tris, pH=7.5), or buffer "C" (0.1M NaCl, 2% phosphoric acid, pH=2). Gel filtration columns were recalibrated with known molecular weight standards with each new running solvent before calculation of the apparent molecular weight for each sampled peptide. Calculated molecular weights from elution profiles of these peptides were usually 2-fold higher in buffer "A" than buffer "B" or "C", as shown in Table 1. "M" indicates monomer, and "D" indicates dimer, formation. N.D. is "not determined".

TABLE 1

| Peptide | Calculated Molecular Weight | | |
| --- | --- | --- | --- |
| | 0.1 M NaCl | 1 M Ammonium Sulfate | 0.1 M NaCl, pH = 2 |
| EPPGGSKVILF (SEQ. ID NO: 8) | 1449 (D) | 604 (M) | 767 (M) |
| FGSSGWVLPSPPGGSKVILF (SEQ. ID NO: 10) | 2123 (D) | 1181 (M) | 1124 (M) |
| YGGFLPPGGSKVILF (SEQ. ID NO: 9) | 1218 (D) | 478 (M) | N.D. |
| LRRASLGGPPGGSKVILF (SEQ. ID NO: 11) | 1825 (D) | 1825 (D) | 966 (M) |
| SKVILFEGGSAS (SEQ. ID NO: 12) | 1722 (D) | 1662 (D) | 646 (M) |
| RQFKVVT (SEQ. ID NO: 13) | 913 (M) | 1050 (M) | N.D. |

One could also use similar methods to identify association peptides that bind one another only under certain environmental conditions, such as in the presence of a particular metal ion or in low pH. One could also use such methods to identify an association peptide that binds to a specific sequence of nucleic acid or that forms a triplex structure with two other homologous or heterologous peptides. Thus, the present invention can be used in a wide variety of applications and to make possible the directed construction of a wide range of molecular complexes.

As can be appreciated from the disclosure above, the present invention has a wide variety of applications. Accordingly, the following examples are offered by way of illustration, not by way of limitation.

EXAMPLE 1

Formation of Dimeric Peptides with Amino-terminal Additions

Peptides with residues added at the amino-terminal sequence of SKVILF (SEQ.ID NO:1) were shown to dimerize on a molecular sieve column (Bio-Gel P-4, from Bio-Rad). Peptides that contained either the Hertz antibody binding motif (YGGFL) (SEQ.ID NO:5), the Kemptide sequence (LRRASLG) (SEQ.ID NO:6), or a ligand (FGSSGWVLPS) (SEQ.ID NO:7) added to the amino-terminal end of the peptide (0.5 mg) were dissolved in 0.5 mL of running The data in Table 1 shows that addition of residues to the SKVILF (SEQ.ID NO:1) motif does not prevent dimer formation. The peptide RQFKVVT (SEQ.ID NO:13) lacks the associative sequence and does not dimerize and so serves as a negative control. Some association peptides form dimers even in the presence of 1M NH₄SO₄/10 mM Tris, pH=7.5. Placing a flexible linker (such as poly G or GGPPGG(SEQ.ID NO:4)) at the amino-terminal end of the association peptide may result in peptides with greater binding affinities as compared with the use of less flexible linkers (such as PPGG(SEQ.ID NO:3)).

EXAMPLE 2

Formation of Dimeric Peptides with Carboxy-terminal Additions

As shown in Table 1, residues can be added to the carboxy-terminus of the association peptide sequence without loss of dimerization Capability. In this Example, peptides containing either the sequence SKVILF (SEQ.ID NO:1) with a free carboxy terminus, SKVILF (SEQ.ID NO:14) with an amide terminus, or SKVILFX, where X is a specified amino acid, with an amide terminus were tested for dimer formation. Peptides with an amide terminus can be used to demonstrate whether a terminal carboxyl group participates in dimerization. A scrambled version of the SKVILF (SEQ.ID NO:1) peptide served as a negative control in these experiments, in which 0.5 mg of peptide was dissolved in 0.5 mL of running buffer, and 0.2–0.4 mL of sample were loaded onto the Bio-Gel P-4 column. After 25 mL were eluted, fractions were collected (67 drops per fraction), and each fraction was analyzed for peptide with a spectrophotometer (at 220 nm, 260 nm, and 280 nm). Columns were recalibrated with known molecular weight standards with each new running solvent before calculation of the apparent molecular weights for the various peptides. Migration profiles of peptides did vary with extensive column use, so internal standards were used continuously during experiments. Elution profiles are shown (calculated molecular weights are in parentheses) in Table 2.

TABLE 2

| Peptide | 0.1 M NaCl, pH = 7.5 | 1 M Ammonium Sulfate |
| --- | --- | --- |
| SKVILF (SEQ ID NO: 1) | 22.5 (1118) | 29 (1002) |
| SKVILF (amide) (SEQ. ID NO: 1) | 33.5 (592) | 43 (572) |
| SKVILFE(amide) (SEQ. ID NO: 15) | 21 (dimer) | 29 (dimer) |
| SKVILFD(amide) (SEQ. ID NO: 16) | 21 (dimer) | 30 (dimer) |
| SKVILFK(amide) (SEQ. ID NO: 17) | 27 (monomer) | 36 (monomer) |
| SKVILFN(amide) (SEQ. ID NO: 18) | 28 (monomer) | 38 (monomer) |
| SKVILFR(amide) (SEQ. ID NO: 19) | 34 (monomer) | 40 (monomer) |
| VSIKFL(scrambled) (SEQ. ID NO: 20) | 29 (monomer) | N.D. |

Tables 1 and 2 demonstrate that the association peptides of the invention that contain the SKVILF (SEQ.ID NO:1) motif and either possess a free carboxy-terminus (at the F residue) or contain an acidic residue (a residue with a free carboxyl group) following the F of the SKVILF (SEQ.ID NO:1) motif can dimerize.

The peptide SKVILFEGGSAS (SEQ.ID NO:12) was constructed to demonstrate that residues can be added to the carboxy-terminus of the SKVILE (SEQ.ID NO:1) motif and that the resulting peptides dimerize. As shown in Table 1 and FIG. 5, the high molecular weight dimer is present in 0.1M NaCl, pH=7.5, as well as 1 NH$_4$SO$_4$/10 mM Tris, pH-7.5. Peptides and proteins formed by extension of the carboxy-terminus of the association peptide SKVILFE (SEQ.ID NO:15)have great binding affinity; some variants form stable dimers in 1M ammonium sulfate. However, acidic (pH=2) conditions (Table 1, FIGS. 3–5) do not promote dimer formation, probably due to the protonation of free carboxy groups, resulting in the inability of peptides to establish an ionic association between free carboxyls and positively charged primary amine groups.

EXAMPLE 3

Dimer Formation in 8M Urea and 6M Guanidine-HCl

Bodenmuller et al., Supra, suggest that the stability of the HA dimer may be similar to that of the streptavidin-biotin complex, which is stable in either 8M Urea or 6M Guanidine-HCl HA peptide and the peptide YGGFLP-PGGSKVILF (SEQ.ID NO:9) were passed through P-4 columns equilibrated in up to 8M Urea in one experiment and 6M guanidine-HCl in another. Elution profiles showed that these peptides eluted as the dimers (high molecular weight) under these conditions.

EXAMPLE 4

Radio-Labeling HA-Peptide Analogs 10 mCi of gamma-labeled $^{32}$P-ATP (Amersham) and protein kinase (Sigma) were used to label the peptide LRRASLGGPPGGSKVILF (SEQ.ID NO:11) (1 mg), which contains the Kemptide sequence, a known phosphorylation site. The phosphorylation reaction was performed, and the phosphorylated peptide was separated from labeled ATP. Purified $^{32}$P-labeled peptide was then diluted and loaded onto the Bio-Gel P-4 column (as described above), and the peptide eluted at a position corresponding to a molecular weight of 1825. The calculated concentration of the eluted dimeric form of the peptide was about 1 nM, indicating a very high binding affinity constant.

EXAMPLE 5

Elution of Peptides from an SKVILF Affinity Column

The peptide CSKVILF (SEQ.ID NO:21) (3 mg) was covalently linked via a dithio-bond to the beads of a Pierce S-Link column according to the manufacturer's protocol, except that the peptide solution was prepared immediately prior to loading onto the S-Link column, because the peptide rapidly precipitates from solution (within 3–5 minutes). A 97.2% coupling efficiency was observed between the column matrix and the peptide.

Various peptides were tested to determine whether or not association occurred on the SKVILF (SEQ.ID NO:1) column matrix according to the general protocol that follows: wash SKVILF (SEQ.ID NO:1) column (2 mL) twice with 4 mL of 1M ammonium sulfate; wash column twice with 4 mL of 2M ammonium sulfate; add resin to a 50 mL conical tube containing 2 stir bars; add 0.5 mL of water to 2–3 mg of peptide to solubilize, then add 0.5 mL of 2M ammonium sulfate to a final concentration of 1M ammonium sulfate and immediately add this solution to the resin; stir for 5 minutes (5 mL total volume); add water (45 mL) dropwise over a period of 60 minutes; add this mixture back to the column and pass through; wash column twice with 2 mL of water; wash column 3 times with 4 mL of water; wash column twice with 2 mL of water; collect the last 2 mL eluting from the column (all fractions=1 mL); wash column twice with 2 mL of 0.1M NaCl, H$_2$PO$_4$, pH=2, and collect fractions; re-equilibrate column in 4 mL of NaHPO$_4$, pH=7.5; and wash the column with water and 0.5% azide.

Determination of the peptide content of collected fractions was determined using a ninhydrin staining procedure. The results are shown below in Table 3.

TABLE 3

| Peptide | Bound to Column? |
| --- | --- |
| SKVILF (SEQ. ID NO: 1) | (+) |
| pGPPGGSKVILF (SEQ. ID NO: 22) | (+) |
| KVILF (SEQ. ID NO: 23) | (−) |
| YGGFM (SEQ. ID NO: 24) | (−) |
| YGGFM(amide) | (−) |
| no peptide added | (−) |

These data show that the SKVILF (SEQ.ID NO:1) motif is required for binding.

EXAMPLE 5

Cloning and Purification of the MBP-HA Protein

The HA sequence was cloned into the carboxy-terminus of the maltose binding protein (MBP). DNA sequences of desired clones confirmed that the coding sequence for the peptide PPGGSKVILF (SEQ.ID NO:25) was correctly integrated to produce the peptide fused to the C-terminus of the MBP protein.

One selected clone was used to generate this MBP-HA protein, which was subsequently purified using an amylose column (according to the protocol supplied by new England Biolabs). The clone was cultured in 1 L of LB-broth containing ampicillin; the culture was grown to an O.D.(600 nm) of 0.5. The compound IPTG (0.4 mM final concentration) was then added to derepress the lac repressor, and after 3 hours, the culture was centrifuged for 15 minutes at 6000 rpm at 10° C. The supernatant was removed, and 40 mL of a buffer composed of 50 mM NaCl, 20 mM Tris, pH=7.5, and 1 mM EDTA were added. The sample was placed in the −20° C. freezer overnight, then thawed and sonicated for 2.5 min. (setting 7.5, 30% duty cycle). The sonicated cell suspension was loaded onto an amylose column (2.5×10.5 cm) and washed with 15 column volumes of the same buffer. MBP-HA protein was eluted from the amylose column using the above buffer containing 10 mM maltose, and 33 mg of purified MBP-HA protein were recovered. The purified MBP-HA was then shown to form dimers in 100 mM NaCl, pH=7.5, under conditions where the MBP protein alone did not.

Although the foregoing invention has been described in some detail by way of illustration and example for purposes of clarity and understanding, it will be apparent that certain changes and modifications may be practiced within the scope of the appended claims.

We claim:

1. A method for joining two or more peptides or proteins, said method comprising the steps of:

(a) attaching an association peptide to either the N- or C-terminus of each of said peptides or proteins to be joined, to form a fusion complex for each of said peptides or proteins to be joined wherein said association peptide comprises the amino acid residue sequence SKVILF (SEQ ID NO:1) and wherein the peptides or proteins to be joined together are attached to said association peptide's amino-terminus or to said association peptide's carboxy terminus, provided that if the peptides or proteins are attached to said carboxy terminus, then a free carboxyl group is positioned adjacent to the F residue of said association peptide; and (b) mixing the fusion complexes resulting from step (a) under conditions that allow said association peptide to dimerize.

2. The method of claim 1, wherein said peptides or proteins to be joined are selected independently from the group of molecules consisting of antibodies, antibody light and heavy chains, catalysts, peptides, polypeptides, proteins, receptors, antibody fragments, and substrates.

3. The method of claim 1, wherein said peptides or proteins to be joined are a catalyst and a substrate.

4. The method of claim 1, wherein one of said peptides or proteins to be joined is a peptide and the other of said peptides or proteins to be joined is a protein.

5. The method of claim 1, wherein said peptides or proteins to be joined are antibody fragments.

6. The method of claim 1, wherein said peptides or proteins to be joined are antibody light and heavy chains.

7. The method of claim 1, wherein said peptides or proteins to be joined are receptors.

8. The method of claim 1, wherein said peptides or proteins to be joined are attached via a linker to said association peptide's amino terminus.

9. The method of claim 8, wherein said linker is GGPPGG (SEQ. ID NO:4) or PPGG (SEQ. ID NO:3).

10. The method of claim 1, wherein one of said peptides or proteins to be joined together is attached to said association peptide's carboxy-terminus and said association peptide also has a second peptide or protein attached to the peptide's amino terminus.

\* \* \* \* \*

SEQUENCE LISTING ( 1 ) GENERAL INFORMATION:

( i i i ) NUMBER OF SEQUENCES: 25

( 2 ) INFORMATION FOR SEQ ID NO:1:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:1:

Ser   Lys   Val   Ile   Leu   Phe
    1                             5

( 2 ) INFORMATION FOR SEQ ID NO:2:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:2:

Gly   Gly   Pro   Pro
    1

( 2 ) INFORMATION FOR SEQ ID NO:3:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:3:

Pro   Pro   Gly   Gly
    1

( 2 ) INFORMATION FOR SEQ ID NO:4:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:4:

```
Gly  Gly  Pro  Pro  Gly  Gly
 1                 5
```

( 2 ) INFORMATION FOR SEQ ID NO:5:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:5:

```
Tyr  Gly  Gly  Phe  Leu
 1                 5
```

( 2 ) INFORMATION FOR SEQ ID NO:6:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:6:

```
Leu  Arg  Arg  Ala  Ser  Leu  Gly
 1                 5
```

( 2 ) INFORMATION FOR SEQ ID NO:7:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:7:

```
Phe  Gly  Ser  Ser  Gly  Trp  Val  Leu  Pro  Ser
 1                 5                          10
```

( 2 ) INFORMATION FOR SEQ ID NO:8:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:8:

```
Glu  Pro  Pro  Gly  Gly  Ser  Lys  Val  Ile  Leu  Phe
 1                 5                          10
```

( 2 ) INFORMATION FOR SEQ ID NO:9:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:9:

```
Tyr Gly Gly Phe Leu Pro Pro Gly Gly Ser Lys Val Ile Leu Phe
 1               5                  10                  15
```

( 2 ) INFORMATION FOR SEQ ID NO:10:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:10:

```
Phe Gly Ser Ser Gly Trp Val Leu Pro Ser Pro Pro Gly Gly Ser Lys
 1               5                  10                  15
Val Ile Leu Phe
                20
```

( 2 ) INFORMATION FOR SEQ ID NO:11:

( i ) SEQUENCE CHARACTERISTICS:
        ( A ) LENGTH: 18 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:11:

```
Leu Arg Arg Ala Ser Leu Gly Gly Pro Pro Gly Gly Ser Lys Val Ile
 1               5                  10                  15
Leu Phe
```

( 2 ) INFORMATION FOR SEQ ID NO:12:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:12:

```
Ser Lys Val Ile Leu Phe Glu Gly Gly Ser Ala Ser
 1               5                  10
```

( 2 ) INFORMATION FOR SEQ ID NO:13:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:13:

```
        Arg  Gln  Phe  Lys  Val  Val  Thr
        1                   5
```

(2) INFORMATION FOR SEQ ID NO:14:

(i) SEQUENCE CHARACTERISTICS:
  (A) LENGTH: 7 amino acids
  (B) TYPE: amino acid
  (C) STRANDEDNESS: single
  (D) TOPOLOGY: linear (ii) MOLECULE TYPE: peptide (xi) SEQUENCE DESCRIPTION: SEQ ID NO:14:

```
        Ser  Lys  Val  Ile  Leu  Phe  Xaa
        1                   5
```

(2) INFORMATION FOR SEQ ID NO:15:

(i) SEQUENCE CHARACTERISTICS:
  (A) LENGTH: 7 amino acids
  (B) TYPE: amino acid
  (C) STRANDEDNESS: single
  (D) TOPOLOGY: linear (ii) MOLECULE TYPE: peptide (xi) SEQUENCE DESCRIPTION: SEQ ID NO:15:

```
        Ser  Lys  Val  Ile  Leu  Phe  Glu
        1                   5
```

(2) INFORMATION FOR SEQ ID NO:16:

(i) SEQUENCE CHARACTERISTICS:
  (A) LENGTH: 7 amino acids
  (B) TYPE: amino acid
  (C) STRANDEDNESS: single
  (D) TOPOLOGY: linear (ii) MOLECULE TYPE: peptide (xi) SEQUENCE DESCRIPTION: SEQ ID NO:16:

```
        Ser  Lys  Val  Ile  Leu  Phe  Asp
        1                   5
```

(2) INFORMATION FOR SEQ ID NO:17:

(i) SEQUENCE CHARACTERISTICS:
  (A) LENGTH: 7 amino acids
  (B) TYPE: amino acid
  (C) STRANDEDNESS: single
  (D) TOPOLOGY: linear (ii) MOLECULE TYPE: peptide (xi) SEQUENCE DESCRIPTION: SEQ ID NO:17:

```
        Ser  Lys  Val  Ile  Leu  Phe  Lys
        1                   5
```

(2) INFORMATION FOR SEQ ID NO:18:

(i) SEQUENCE CHARACTERISTICS:
  (A) LENGTH: 7 amino acids
  (B) TYPE: amino acid
  (C) STRANDEDNESS: single
  (D) TOPOLOGY: linear (ii) MOLECULE TYPE: peptide (xi) SEQUENCE DESCRIPTION: SEQ ID NO:18:

```
      Ser  Lys  Val  Ile  Leu  Phe  Asn
      1                 5
```

(2) INFORMATION FOR SEQ ID NO:19:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:19:

```
      Ser  Lys  Val  Ile  Leu  Phe  Arg
      1                 5
```

(2) INFORMATION FOR SEQ ID NO:20:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:20:

```
      Val  Ser  Ile  Lys  Phe  Leu
      1                 5
```

(2) INFORMATION FOR SEQ ID NO:21:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:21:

```
      Cys  Ser  Lys  Val  Ile  Leu  Phe
      1                 5
```

(2) INFORMATION FOR SEQ ID NO:22:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:22:

```
      Gly  Pro  Pro  Gly  Gly  Ser  Lys  Val  Ile  Leu  Phe
      1                 5                      10
```

(2) INFORMATION FOR SEQ ID NO:23:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:23:

```
    Lys  Val  Ile  Leu  Phe
    1                    5
```

( 2 ) INFORMATION FOR SEQ ID NO:24:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:24:

```
    Tyr  Gly  Gly  Phe  Met
    1                    5
```

( 2 ) INFORMATION FOR SEQ ID NO:25:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:25:

```
    Pro  Pro  Gly  Gly  Ser  Lys  Val  Ile  Leu  Phe
    1              5                        10
```